(12) United States Patent
Lin et al.

(10) Patent No.: US 9,737,570 B2
(45) Date of Patent: Aug. 22, 2017

(54) METHOD AND COMPOSITION OF INDUCING HAIR FOLLICLE NEOGENESIS

(71) Applicants: National Taiwan University, Taipei (TW); Academia Sinica, Taipei (TW)

(72) Inventors: Sung-Jan Lin, Taipei (TW); Mai-Yi Fan, Taipei (TW); Yu-Ju Chen, Taipei (TW); Chia-Feng Tsai, Taipei (TW)

(73) Assignees: National Taiwan University, Taipei (TW); Academia Sinica, Taipei (TW)

( * ) Notice: Subject to any disclaimer, the term of this patent is extended or adjusted under 35 U.S.C. 154(b) by 60 days.

(21) Appl. No.: 14/657,582

(22) Filed: Mar. 13, 2015

(65) Prior Publication Data

US 2016/0129046 A1 May 12, 2016

(30) Foreign Application Priority Data

Nov. 7, 2014 (TW) .............................. 103138787 A (51) Int. Cl.
| | | |
|---|---|---|
| *A61K 35/36* | (2015.01) | |
| *A61K 35/33* | (2015.01) | |
| *A61K 9/00* | (2006.01) | |
| *A61K 38/17* | (2006.01) | |
| *A61K 38/39* | (2006.01) | |
| *A61K 8/00* | (2006.01) | |

(52) U.S. Cl.
CPC ................ *A61K 35/36* (2013.01); *A61K 8/00* (2013.01); *A61K 9/0019* (2013.01); *A61K 35/33* (2013.01); *A61K 38/1709* (2013.01); *A61K 38/1732* (2013.01); *A61K 38/39* (2013.01)

(58) Field of Classification Search
CPC .......... A61K 2300/00; A61K 47/48284; A61K 31/138; A61K 31/496; A61K 31/517; A61K 31/737; A61K 39/395; A61K 45/06; A61K 2039/55588; A61K 2039/57; A61K 38/00; A61K 38/193; A61K 39/3955; A61K 39/40; A61K 35/33; A61K 35/36; A61K 38/1709; A61K 38/1732; A61K 38/39; A61K 8/00; A61K 9/0019; C07K 14/4713; C12N 2501/11; C12N 2501/119; C12N 2501/12; C12N 2501/148; C12N 2501/15; C12N 2501/155; C12N 2506/02; C12N 5/0676
See application file for complete search history.

(56) References Cited

U.S. PATENT DOCUMENTS

2014/0079686 A1* 3/2014 Barman ............... A61K 8/4953
424/94.67

OTHER PUBLICATIONS

Sabrina Mai-Yi Fan, "Inducing hair follicle neogenesis by defined extracellular factors", Journal of Investigative Dermatology, May 2014, vol. 134 Supplement 1.

* cited by examiner

*Primary Examiner* — Debbie K Ware
(74) *Attorney, Agent, or Firm* — WPAT, P.C., Intellectual Property Attorneys; Anthony King (57) ABSTRACT

The present invention provides a method of inducing hair follicle neogenesis in the skin of a subject in need by transplanting the mixture of the skin extract or the composition with epidermal cells or fibroblasts into the subject. The skin extract of the present invention is obtained by mincing and mixing a skin tissue with phosphate buffer solution, thawing the skin tissue after freeze. The composition of the present invention includes at least lumican, galectin-1 and apolipoprotein A-I.

10 Claims, 6 Drawing Sheets

METHOD AND COMPOSITION OF INDUCING HAIR FOLLICLE NEOGENESIS

CROSS-REFERENCE TO RELATED APPLICATION

This application claims the priority of Taiwanese patent application No. 103138787, filed on 7 Nov. 2014, which is incorporated herewith by reference.

BACKGROUND OF THE INVENTION

1. Field of the Invention

The invention relates to a method of inducing hair follicle neogenesis by using a skin extract. More particularly, the invention also relates to a method of inducing hair follicle neogenesis by using a protein composition.

2. The Prior Arts

Prior arts for hair follicle (HF) regeneration can be classified into three methods, including (i) implantation of a large number of hair follicle dermal papilla cells, (ii) induction of HF neogenesis by creating wounds in the skin, and (iii) transplantation of folliculoids that are generated in vitro. In the first method, dermal papilla cells (DP cells) must maintain aggregate form during growth to retain function of HFs. Many researches employ this concept with various approaches to promote aggregation of large amount of DP cells then transplanting into the skin of animals. However, the transplantation site of cultured DP cells must be in close proximity to the epidermis to induce HF neogenesis, which increases difficulty in clinical application. In the second method, a suitable size of surgical cut is created on the animal skin to generate an environment that simulating HF development at the embryonic stage. Neogenesis of HFs and hair shafts will appear at the cut site and the regenerated HFs has the characteristics of hair cycle. However, part of the skin must be excised when this method is used and thus clinically unsuitable. Furthermore, this method has not been successfully proved in human. The third method is production of HF microtissues in vitro using polymers or hydrophilic gel as substratum. However, preparation process of such substratum is complicate and successful induction of HF neogenesis is achieved when embryonic or newborn cells are employed.

The drug for treating baldness on the market does not have good effect for the patients with severe hair loss and alopecia areata. So far the method of inducing hair follicle neogenesis in adult is to culture autologous hair follicle dermal papilla forming a cell cluster, and to transplant the cell cluster under the skin inducing hair follicle neogenesis. However, the method of inducing hair follicle neogenesis is too inefficient to be useful in treatment.

In hair follicle neogenesis process, it needs both a certain amount of hair follicle dermal papilla cells and epidermal cells to have the ability of inducing hair follicle after mixing each other. Therefore, according to the concept, many studies intend to mix hair follicle dermal papilla cells and epidermal cells in different proportions, then to transplant into a patient needed. However, it spends more time and cost obtaining the patient's hair follicle first and isolating hair follicle dermal papilla cells for a large-scale culture in the process. Thus, for the purpose of saving time and cost, it is necessary to develop an efficient and convenient method of inducing hair follicle neogenesis.

SUMMARY OF THE INVENTION

To solve the problem, the present invention provides a method of inducing hair follicle neogenesis, which comprising mixing the skin extract with epidermal cells and injecting or dressing to an open wound, which can induce hair follicle regeneration. The skin extract of present invention can be used to culture with fibroblasts in vitro for three days, and the fibroblasts can induce hair follicle neogenesis after transplanting to a subject. Moreover, detailed analysis of the skin extract is included three main proteins, and the three proteins directly mix with fibroblasts or epithelial cells can induce hair follicle neogenesis.

One aspect of the present invention is related to a method of inducing hair follicle neogenesis in the skin of a subject in need thereof, comprising the steps of: a. providing a skin extract, wherein the skin extract is obtained from mincing and mixing a skin tissue derived from the subject with phosphate buffer solution (PBS) to form a skin tissue solution, thawing the skin tissue solution after overnight freeze; b. mixing the skin extract with a cell to form a mixture, wherein the cell is a epithelial cell or a fibroblast derived from the subject; and c. transplanting the mixture into the subject, and the density of the mixture of step b is $1.0 \times 10^4$ to $2.0 \times 10^4$ cells per microliter ($\mu$L) of the skin extract.

In one embodiment, the ratio of the skin tissue and PBS is 1 mg of the skin tissue: 400 $\mu$L to 500 $\mu$L of PBS.

In one embodiment, the skin extract freezes at $-70°$ C. to $-120°$ C. at least over 8 hours.

In one embodiment, the skin extract comprises galectin-1, lumican, apolipoprotein A-I, gelsolin, fibronectin and fibrinogen, or the skin extract comprises galectin-1, lumican and apolipoprotein A-I.

In one embodiment, the transplanting step is to inject the mixture to a wound of the subject.

In one embodiment, the mixture further processes a collagen treatment to form a collagen gel, and the transplanting step is to cover the collagen gel to a wound of the subject.

Another aspect of the present invention is related to a composition of inducing hair follicle neogenesis, comprising lumican, galectin-1 and apolipoprotein, and the composition can further comprises gelsolin, fibronectin and fibrinogen.

In one embodiment, the composition is dissolved in PBS, and the ratio of the composition and PBS is 200 ng to 600 ng of the composition: 150 $\mu$L to 250 $\mu$L of PBS.

Another aspect of the present invention is related to a method of inducing hair follicle neogenesis in the skin of a subject in need thereof, comprising administrating the above-mentioned compositions and an epithelial cell to the subject; wherein the epithelial cell derives from the subject.

In one embodiment, the composition further comprises gelsolin, fibronectin and fibrinogen.

In one embodiment, the composition is dissolved in PBS, the ratio of the composition and PBS is 200 ng to 600 ng of the composition: 150 $\mu$L to 250 $\mu$L of PBS.

In one embodiment, the administrating step is to inject or dress to a wound of the subject.

The present invention provides a skin extract and composition of inducing hair follicle neogenesis which can induce epithelial cells to regenerate the hair follicle without hair follicle dermal papilla cells. Because the skin extract or the composition of the present invention mixing with cells (fibroblasts or epithelial cells) can directly transplant into a subject, it does not require the current step of culturing the cluster of hair follicle dermal papilla cells. The skin extract and specific proteins in the skin extract of the present invention can induce hair follicle neogenesis.

Therefore, the method of the present invention can omit the current step of obtaining and culturing hair follicle dermal papilla cells from a subject. And the method of the present invention only needs to take few amounts of the skin extract and epidermal cells or fibroblasts, which can effectively induce hair follicle neogenesis. Furthermore, in the present invention, the process manufacturing process of the composition for inducing hair follicle neogenesis does not need sophisticated equipment, complex technology and process, to reach the purpose of reducing the cost.

Thus, the skin extract or composition of the present invention is not only applied topically to promote a wound induced hair follicle neogenesis but also applied in artificial dermis to induce hair follicle neogenesis. In addition, the skin extract or composition of the present invention can be cultured with fibroblasts in vitro make fibroblasts have the ability of inducing hair follicle neogenesis.

The detailed technology and above preferred embodiments implemented for the present invention are described in the following paragraphs accompanying the appended drawings for people skilled in this field to well appreciate the features of the claimed invention.

BRIEF DESCRIPTION OF THE DRAWINGS

FIG. 1 A to FIG. 1C show that the skin extract of the present invention can induce the formation of hair follicle structure; black arrow indicates hair follicle structure.

DETAILED DESCRIPTION OF THE PREFERRED EMBODIMENT

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention.

Unless otherwise defined, all technical and scientific terms used herein have the same meaning as commonly understood by one of ordinary skill in the art to which this invention pertains. In the case of conflict, the present document, including definitions will control.

As used herein, "hair follicle dermal papilla cells" means the structure of hair bulb in the hair follicle, which covers a group of fibroblasts.

As used herein, the terms "inducing hair follicle neogenesis", "inducing hair follicle regeneration" or "induce to regenerate hair follicle" mean to induce epidermal cell regenerating hair follicle.

The method of the present invention by using the skin extract or composition can be applied on the wound to induce hair follicle neogenesis, the method does not require to prior to culturing the hair follicle dermal papilla cells for transplantation. Also, the present invention detects the core proteins in the skin extract, and mixing the core protein to form the composition of the present invention, which also have the ability of inducing hair follicle neogenesis. Hereinafter, the method of the present invention has validated that the skin extract or the composition can induce hair follicle neogenesis without hair follicle dermal papilla cells.

Example 1

Preparing the Skin Extract for Inducing the Ability Hair Follicle Regeneration

Isolating rat embryos (wistar rat; C57BL/6 mice, either sex, embryos at embryonic days 14.5 to 19.5) skin, then mincing and mixing 1 mg skin tissue with 400 μL to 500 μL phosphate buffer solution (PBS); thawing the mixture after overnight at −80° C.; pumping the mixture back and forth several times in the needle to ensure the skin tissue completely damaged.

Example 2

Method of Inducing Hair Follicle Neogenesis

In the present invention, there are five methods to validate that the skin extract in Example 1 either mixing with fibroblasts or epithelial cells can induce a subject to regenerate hair follicle. The fibroblasts or epithelial cells can be respectively obtained by the methods as follows. Fibroblasts: isolating the dermal tissues from rat skin (C57BL/6 mice, 4 to 7 weeks), culturing the dermal tissues in Dulbecco's modified Eagle's medium (DMEM) supplemented with 10% fetal bovine serum (FBS) until the third generation, and that is called the fibroblasts of the present invention. Epidermal cells: obtaining the tissue from the rat (C57BL/6 mice, either sex, neonatal rat) back skin, removing the muscle and adipose cell from the tissue, placing the tissue in 5 U dispase at 37° C. for 1 hr, separating the epidermis from dermis after the dispase reaction, scraping the epidermal cells with round tip tweezer and adding the DMEM with 10% FBS to the epidermal cells to neutralizing the dispase reaction, then obtaining the epidermal cells by passing through a 40 μm filter, that is called the epidermal cells of the present invention.

Figure 1A:
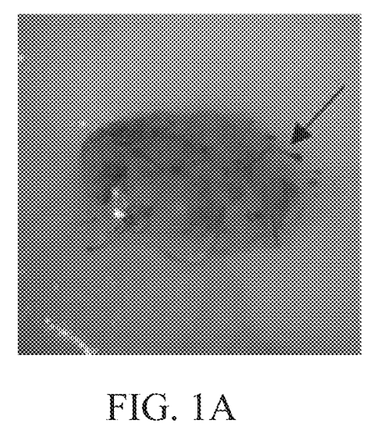
Figure 1B:
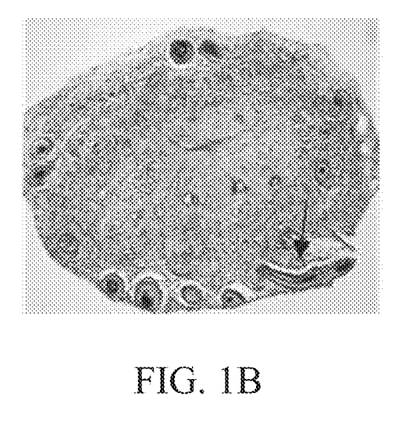
Figure 1C:
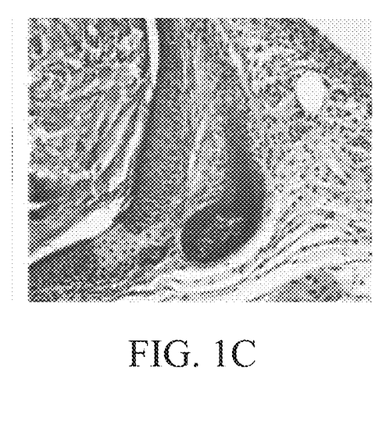

1. Mixing $1.0 \times 10^6$ to $2.0 \times 10^6$ the epidermal cells with 100 μL the skin extract (total protein is 250 ng) and transplanting the mixture into subcutaneous skin of the nude rat. After 4 weeks, FIG. 1A shows that the formation of hair follicle structure in subcutaneous skin of the nude rate. FIG. 1B and FIG. 1C show the formation of hair follicle structure by using hematoxylin and eosin stain.

Figure 2:
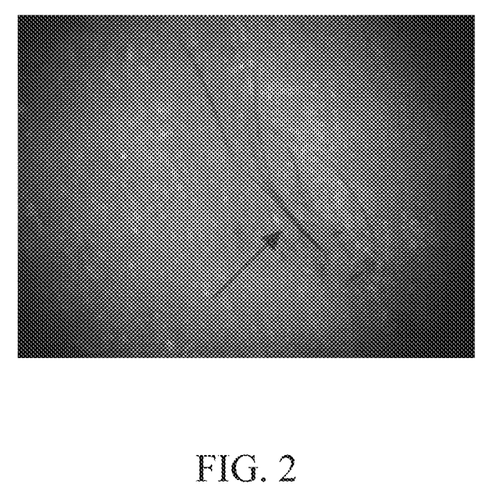
FIG. 2 shows that the skin extract of the present invention can induce the formation of hair follicle structure; black arrow indicates hair follicle structure.

2. Cutting a 1 cm×1 cm wound on nude rat back, dressing a 3 M Tegaderm transparent medical dressing on the wound to keep it from air and pollutant, injecting the mixture of $1.0 \times 10^6$ to $2.0 \times 10^6$ the epidermal cells and the skin extract to the wound by using 18 G needle. After 4 weeks, FIG. 2 shows that the formation of hair follicle structure in subcutaneous skin of the nude rate.

Figure 3:
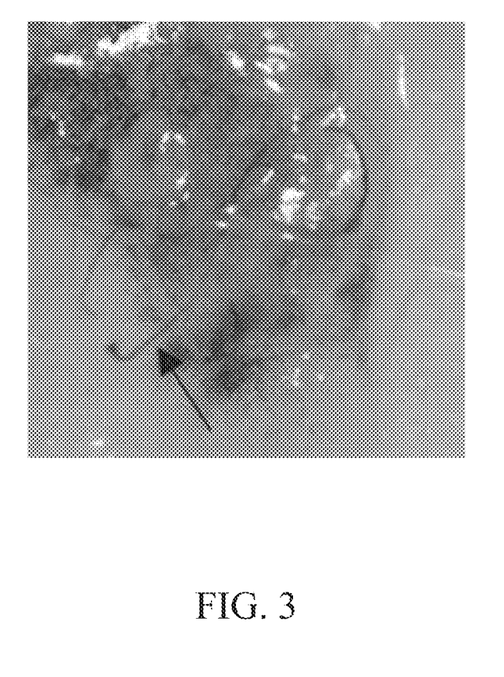
FIG. 3 shows that the skin extract of the present invention can induce the formation of hair follicle structure; black arrow indicates hair follicle structure.

3. Adding the skin extract to the fibroblasts culture dish containing the mixing medium of 1:1 (v:v) ratio of DMEM and Ham's F-12 supplemented with 10% FBS, culturing the fibroblasts at 37° C. in 5% $CO_2$ incubator for 3 days. Then collecting $1.0\times10^6$ to $2.0\times10^6$ the fibroblasts after induction for three days to mix with $1.0\times10^6$ to $2.0\times10^6$ the epidermal cells of neonatal rat, transplanting the mixture into subcutaneous skin of the nude rat not necessarily to form a structure similar to the hair follicle cell cluster. After 4 weeks, FIG. 3 shows that the formation of hair follicle structure in subcutaneous skin of the nude rate.

Figure 4:
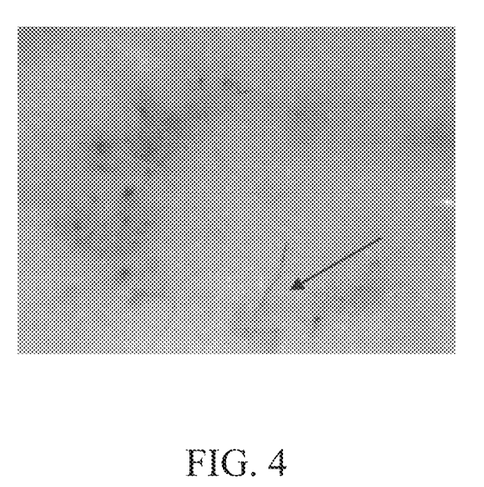
FIG. 4 shows that the skin extract of the present invention can induce the formation of hair follicle structure; black arrow indicates hair follicle structure.

4. Culturing the fibroblasts in the collagen gel as dermal equivalent model. Adding the skin extract to the fibroblasts culture dish containing the mixing medium of 1:1 (v:v) ratio of DMEM and Ham's F-12 supplemented with 10% FBS, culturing the fibroblasts at 37° C. in 5% $CO_2$ incubator for 3 days. Cutting a 1 cm×1 cm wound on nude rat back, covering a collagen gel on the wound and then dressing a 3 M Tegaderm transparent medical dressing, injecting the mixture of $1.0\times10^6$ to $2.0\times10^6$ the epidermal cells and the skin extract to the wound by using 18 G needle. After 4 weeks, FIG. 4 shows that the formation of hair follicle structure in the nude rate skin.

Figure 5:
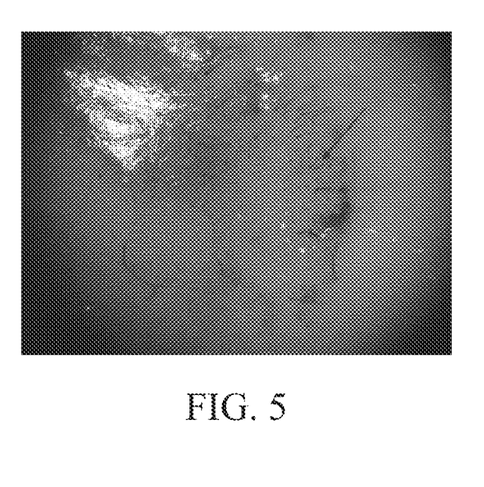
FIG. 5 shows that the skin extract of the present invention can induce the formation of hair follicle structure; black arrow indicates hair follicle structure.

5. Manufacture an artificial dermis by culturing the mixture of $1.0\times10^6$ to $2.0\times10^6$ the fibroblasts with the skin extract in the collagen in vitro. Cutting a 1 cm×1 cm wound on nude rat back, covering a collagen gel on the wound and then dressing a 3 M Tegaderm transparent medical dressing to keep it from air and pollutant, injecting the mixture of $1.0\times10^6$ to $2.0\times10^6$ the epidermal cells and the skin extract to the wound by using 18 G needle. After 4 weeks, FIG. 5 shows that the formation of hair follicle structure in the nude rate skin.

The five different methods validate that the skin extract in Example 1 either mixing with fibroblasts or epithelial cells can induce a subject to regenerate hair follicle.

Example 3

Mixing the Specific Proteins Contained in the Skin Extract to Induce Hair Follicle Neogenesis In the present invention, the main proteins in the skin extract are galectin-1, lumican, apolipoprotein A-I, gelsolin, fibronectin and fibrinogen detected by Mass spectrometry.

Figure 6:
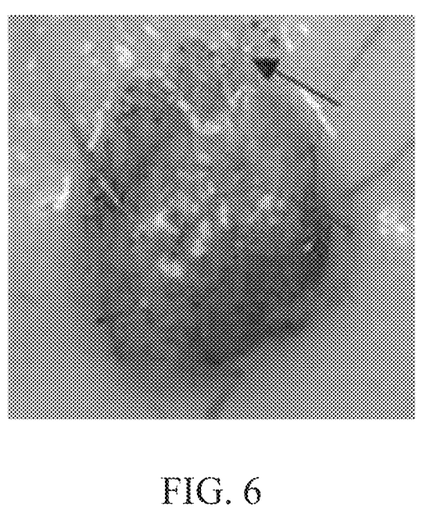
FIG. 6 shows that the six protein composition of the present invention can induce the formation of hair follicle structure; black arrow indicates hair follicle structure.

The present invention provides the six protein composition. Taking 100 ng above-mentioned six proteins individually to 150 μL to 250 μL PBS and mixing to form the six protein composition, then mixing the six protein composition with epidermal cells to transplant into subcutaneous skin of the nude rat. After 4 weeks, FIG. 6 shows that the formation of hair follicle structure in subcutaneous skin of the nude rate.

Figure 7:
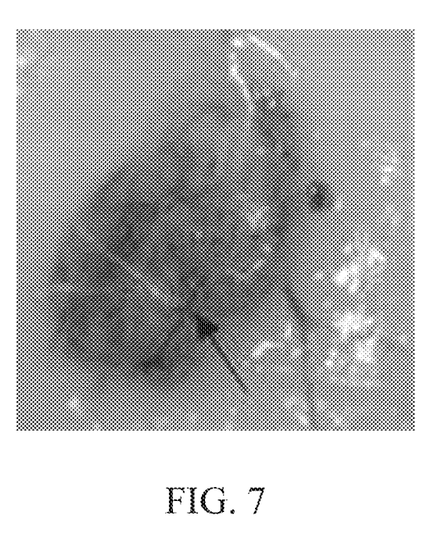
FIG. 7 shows that the three protein composition of the present invention can induce the formation of hair follicle structure; black arrow indicates hair follicle structure.

The present invention further provides three protein composition simplified from the six protein composition. Taking 100 ng three proteins (galectin-1, lumican and apolipoprotein A-I) individually to 150 μL to 250 μL PBS and mixing to form the three protein composition, then mixing the three protein composition with epidermal cells to transplant into subcutaneous skin of the nude rat. After 4 weeks, FIG. 7 shows that the formation of hair follicle structure in subcutaneous skin of the nude rate. These results all validate the protein composition has the ability of inducing hair follicle neogenesis.

Comparable Example 1

Figure 8:
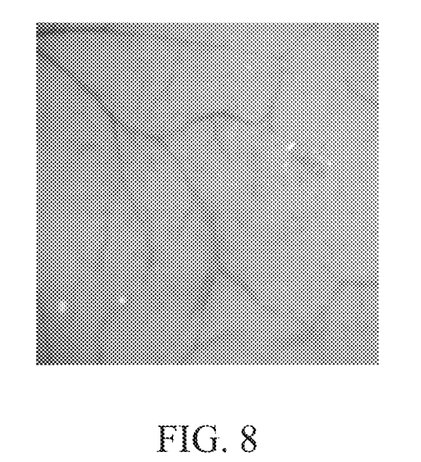
FIG. 8 shows that a single protein (galectin-1) cannot induce the formation of hair follicle structure; black arrow indicates hair follicle structure.
Figure 9:
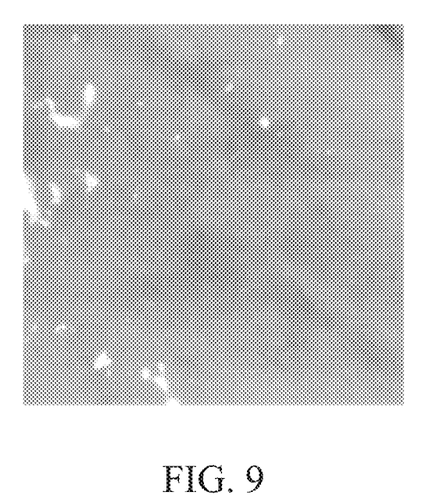
FIG. 9 shows that a single protein (lumican) cannot induce the formation of hair follicle structure.
Figure 10:
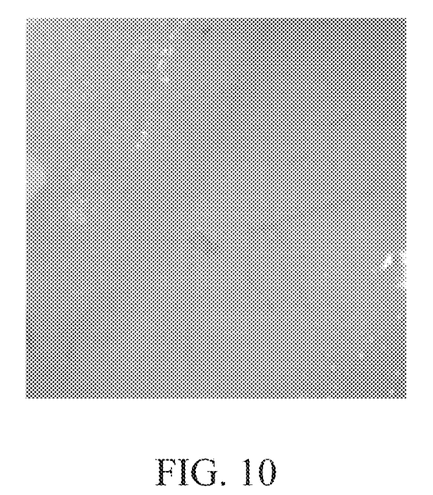
FIG. 10 shows that a single protein (apolipoprotein A-I) cannot induce the formation of hair follicle structure.

Three Single Protein (Galectin-1, Lumican or Apolipoprotein A-I) to Test Hair Follicle Neogenesis Also, the present invention provides three single proteins (galectin, lumican or apolipoprotein) to induce hair follicle neogenesis as comparable example. Mixing 100 ng protein (galectin-1, lumican or apolipoprotein A-I) to 150 μL to 250 μL PBS, mixing the protein with the epithelial cell to form a mixture, and transplanting the mixture into subcutaneous skin of the nude rat, respectively. After 4 weeks, FIG. 8 shows that the result of galectin-1, FIG. 9 shows the result of lumican and FIG. 10 shows the result of apolipoprotein A-I. These results show that three single proteins (galectin, lumican or apolipoprotein) cannot induce hair follicle neogenesis.

The present invention provides a method or a composition of inducing hair follicle neogenesis which can induce epithelial cells to regenerate the hair follicle without hair follicle dermal papilla cells. Because the skin extract or the composition of the present invention mixing with cells (fibroblasts or epithelial cells) can directly transplant into a subject, it does not require the current step of culturing the cluster of the hair follicle dermal papilla cells. Therefore, the skin extract and the composition of the present invention can omit the step of culturing hair follicle dermal papilla cells in a large-scale, which can save a lot of time and cost for treating hair loss.

Thus, the method of the present invention is to apply the skin extract and the composition to an open wound, which not only promotes the wound healing but also induces hair follicle neogenesis. In addition, manufacturing an artificial by adding the skin extract of the present invention and fibroblasts or epidermal cells to collagen, this also can regenerate new hair follicle after transplantation.

What is claimed is:

1. A method of inducing hair follicle neogenesis in the skin of a subject in need thereof, comprising the steps of:
   a. providing a skin extract, wherein the skin extract is obtained from mincing and mixing a skin tissue derived from the subject with phosphate buffer solution (PBS) to form a skin tissue solution, thawing the skin tissue solution after overnight freeze;
   b. mixing the skin extract with a cell to form a mixture, wherein the cell is a epithelial cell or a fibroblast derived from the subject; and
   c. transplanting the mixture into the subject.

2. The method according to claim 1, wherein the ratio of the skin tissue and PBS is 1 mg of the skin tissue: 400 μL to 500 μL of PBS.

3. The method according to claim 1, wherein the skin extract freezes at −70° C. to −120° C.

4. The method according to claim 1, wherein the skin extract freezes at least over 8 hours.

5. The method according to claim 1, wherein the density of the mixture of step b is $1.0\times10^4$ to $2.0\times10^4$ cells per microliter (μL) of the skin extract.

6. The method according to claim 1, wherein the skin extract comprises galectin-1, lumican, apolipoprotein A-I, gelsolin, fibronectin and fibrinogen.

7. The method according to claim 1, wherein the skin extract comprises galectin-1, lumican and apolipoprotein A-I.

8. The method according to claim 1, wherein the transplanting step is to inject the mixture to a wound of the subject.

9. The method according to claim 1, wherein the step b further processes a collagen treatment to form a collagen gel.

10. The method according to claim 9, wherein the transplanting step is to cover the collagen gel to a wound of the subject.

\* \* \* \* \*